United States Patent
Kilian et al.

(10) Patent No.: US 8,440,805 B2
(45) Date of Patent: May 14, 2013

(54) ALGAL DESATURASES

(75) Inventors: Oliver Kilian, Alameda, CA (US);
Bertrand Vick, Berkeley, CA (US)

(73) Assignee: Aurora Algae, Inc., Hayward, CA (US)

( * ) Notice: Subject to any disclaimer, the term of this patent is extended or adjusted under 35 U.S.C. 154(b) by 0 days.

(21) Appl. No.: 13/458,914

(22) Filed: Apr. 27, 2012

(65) Prior Publication Data

US 2012/0277417 A1 Nov. 1, 2012

Related U.S. Application Data

(60) Provisional application No. 61/480,353, filed on Apr. 28, 2011.

(51) Int. Cl.
*C07H 21/04* (2006.01)
*C12N 9/00* (2006.01)

(52) U.S. Cl.
USPC ......................................... 536/23.2; 435/183

(58) Field of Classification Search ................. 536/23.2; 435/183
See application file for complete search history.

(56) References Cited

U.S. PATENT DOCUMENTS

| | | |
|---|---|---|
| 3,962,466 A | 6/1976 | Nakabayashi |
| 5,105,085 A | 4/1992 | McGuire et al. |
| 5,661,017 A | 8/1997 | Dunahay et al. |
| 5,668,298 A | 9/1997 | Waldron |
| 5,723,595 A * | 3/1998 | Thompson et al. ........... 536/23.6 |
| 6,027,900 A | 2/2000 | Allnutt et al. |
| 6,143,562 A | 11/2000 | Trulson et al. |
| 6,297,054 B1 | 10/2001 | Maliga et al. |
| 6,831,040 B1 | 12/2004 | Unkefer et al. |
| 7,244,609 B2 | 7/2007 | Drocourt et al. |
| 7,410,637 B2 | 8/2008 | Sayre et al. |
| 7,547,551 B2 | 6/2009 | Schuler et al. |
| 8,039,230 B2 | 10/2011 | Otte et al. |
| 8,119,859 B2 | 2/2012 | Vick et al. |
| 8,314,228 B2 | 11/2012 | Kilian et al. |
| 8,318,482 B2 | 11/2012 | Vick et al. |
| 2003/0143743 A1 | 7/2003 | Schuler et al. |
| 2003/0211089 A1 | 11/2003 | Sayre et al. |
| 2005/0064577 A1 | 3/2005 | Berzin |
| 2005/0124010 A1 | 6/2005 | Short et al. |
| 2006/0101535 A1 | 5/2006 | Forster et al. |
| 2006/0166243 A1 | 7/2006 | Su et al. |
| 2006/0166343 A1 | 7/2006 | Hankamer et al. |
| 2007/0178451 A1 | 8/2007 | Deng et al. |
| 2008/0118964 A1 | 5/2008 | Huntley et al. |
| 2008/0120749 A1 | 5/2008 | Melis et al. |
| 2008/0194029 A1 | 8/2008 | Hegemann et al. |
| 2008/0293132 A1 | 11/2008 | Goldman et al. |
| 2009/0061493 A1 | 3/2009 | Trimbur et al. |
| 2009/0148931 A1 | 6/2009 | Wilkerson et al. |
| 2009/0317878 A1 | 12/2009 | Champagne et al. |
| 2009/0317904 A1 | 12/2009 | Vick et al. |
| 2009/0325270 A1 | 12/2009 | Vick et al. |
| 2010/0210832 A1 | 8/2010 | Kilian et al. |
| 2010/0323387 A1 | 12/2010 | Bailey et al. |
| 2011/0059495 A1 | 3/2011 | Bailey et al. |
| 2011/0091977 A1 | 4/2011 | Kilian et al. |
| 2012/0190115 A1 | 7/2012 | Kilian et al. |

FOREIGN PATENT DOCUMENTS

| | | |
|---|---|---|
| WO | 2004106238 A2 | 12/2004 |
| WO | 2008060571 A2 | 5/2008 |
| WO | 2009149470 A1 | 12/2009 |
| WO | 2010011335 A1 | 1/2010 |
| WO | 2011011463 A2 | 1/2011 |
| WO | 2011049995 A1 | 4/2011 |

OTHER PUBLICATIONS

Abe et al. AG610981, Musmusculus molossinus DNA 2004.
Kopczynski et al.CO268749, Drosophila melanogaster cDNA clone EK092604 2004.
Chen et al. Conditional Production of a Functional Fish Growth Hormonal in the Transgenic Line of Nannochloropsis oculata (Eustigamatophyceae). J. Phycol. Jun. 2008. vol. 44. No. 3. pp. 768-776. Especially abstract.
Csogor et al. "Light distribution in a novel photobioreactor—modeling for optimization" Journal of Applied Phycology, vol. 13, p. 325-333, May 2001, Entire document, especially: abstract; p. 110, col. 1-2 [online]. Retrieved from the Internet on [Oct. 5, 2010]. Retrieved from: <URL:http://www.springerlink.com/content/p77j66g3j2133522/fulltext.pdf.
Endo et al. "Inactivation of Blasticidin S by Bacillus Cereus II. Isolation and Characterization of a Plasmid, pBSR 8, from Bacillus Cereus," The Journal of Antibiotics 41 (2): 271-2589-2601, 1988 MM.
Genbank Accession No. U71602 (*Nannochloropsis* sp. Violaxnthin/chlorophyll a binding preotein precursor (NANVCP) mRNA), 1996 (NPL 0017).
Hallmann et al., "Genetic Engineering of the Multicellular Green Alga Volvox: A Modified and Multiplied Bacterial Antibiotic Resistance Gene as a Dominant Selectable Marker" The Plant Journal 17(1): 99-109 (Jan. 1999).
Janssen, M. "Photosynthetic efficiency of *Dunaliella tertiolecta* under short light/dark cycles" Enzyme and Microbial Technology, 29, 2001, pp. 298-305.
Janssen et al. "Enclosed outdoor photobioreactors: light regime, photosynthetic efficiency, scale-up, and future prospects" Biotechnology and Bioengineering, vol. 81, No. 2, p. 193-210, Jan. 20, 2003, Entire document, especially: Fig 4, p. 198 [online]. Retrieved from the Internet on [Oct. 5, 2010]. Retrieved from: <URL: http://onlinelibrary.wiley.com/doi/10.1002bit.10468/pdf.
Kindle et al. "Stable Nuclear Transformation of Chlamydomonas Using the Chlamydomonas Gene for Nitrate Reductase" The Journal of Cell Biology 109 (6, part 1): 2589-2601, 1989 MM.
Molnar et al. Highly specific gene silencing by artificial microRNAs in the unicellular alga *Chlamydomonas reinhardtii*. Plant Jour. ePub Jan. 17, 2009 vol. 58 No. 1 pp. 157-164. Especially abstract.
Nelson et al. Targeted Disruption of the NIT8 Gene in *Chlamydomonas reinhardtii*. Mol. Cell Bio. Oct. 1995. vol. 15, No. 10, pp. 5762-5769. Especially abstract and pp. 5763 left col. Para. 2, 1995 MM.

(Continued)

*Primary Examiner* — Maryam Monshipouri
(74) *Attorney, Agent, or Firm* — Carr & Ferrell LLP

(57) ABSTRACT

Provided herein are exemplary isolated nucleotide sequences encoding polypeptides having desaturase activity, which utilize fatty acids as substrates.

11 Claims, 11 Drawing Sheets

OTHER PUBLICATIONS

Prein et al. "A Novel Strategy for Constructing N-Terminal Chromosomal Fusions to Green Fluorescent Protein in the Yeast *Saccharomyces cerevisiae*" FEBS Letters 485 (2000) 29-34, 2000 MM.
Roessler et al. (Generic Engineering Approaches for Enhanced Production of Biodiesel Fuel from Microalgae, ACS Symposium Series; American Chemical Society, 1994; p. 255-270).
Saenz, M.E. "Effects of Technical Grade and a Commercial Formulation of Glyphosate on Algal Population Growth" Bulletin of Environmental Contamination Toxicology, 1997, pp. 638-644 vol. 59.
Schiedlmeier et al., "Nuclear Transformation of Volvox Carteri" Proceedings of the National Academy of Sciences USA 91(11): 5080-5084 (May 1994).
Shi et al. Analysis of expressed sequence tags from the marine microalga *Nannochloropsis oculata* (eustigmatophyceae) J Phycol v 44, p. 99-102 (2008).
Strzepek et al., "Photosynthetic architecture differs in coastal and oceanie diatoms" Nature vol. 431, p. 689-692, Oct. 7, 2004. Entire document, especially: abstract, p. 689, col. 2; p. 691, Table 1 [online] Retrieved from the Internet on [Oct. 5, 2010]. Retrieved from: URL:http://www.nature.com/nature/journal/v431/n7009/pdf/nature02954.pdf.
Sukenik et al (Journal of Psychology. Jun. 2000; 36(3): 563-570).
Thiel et al. Transformation of a Filamentous Cyanobacterium by Electroporation. Journal of Bacteriology. Oct. 1989, vol. 171, No. 10, pp. 5743-5746, especially p. 5743, abstract, p. 5744, left column, first paragraph, Fig 1, Abstract only.
Wendland et al. "PCR-Based Methods Facilitate Targeted Gene Manipulations and Cloning Procedures" Curr.Gen. (2003) 44:115-123.
Zittelli et al. "Mass cultivation of *Nannochloropsis* sp. In annular reactors" Journal of Applied Phycology vol. 15, p. 107-113, Mar. 2003. Entire document, especially: abstract; p. 110, col. 1-2 [online]. Retrieved from the Internet on [Oct. 5, 2010]. Retrieved from: <URL: http://www.springerlink.com/content/v77772k1mp081775/fulltext.pdf.
Krienitz et al., Phycologia, 2000, vol. 39, No. 3, Abstract, abstract only.
Sukenik et al. Characterization of a Gene Encoding the Light-Harvesting Violaxanthin-Cholorphyll Protein of *Nannochloropsis* SP. (*Eustigmatophyceae*) J. Phycal. 36, 563-570 (2000).
Hallmann, Armin, Algal Transgenics and Biotechnology, Transgenic Plan Journal 81-98 2007 Global Science Books.
Rocha et al., Growth aspects of the marine microalga *nannochloropsis gaditana*, Biomolecular Engineering, 2003, vol. 20 p. 237-242.
MacIntyre et al., Primary Production by suspended and benthic microalgae in a turbid estuary: time-scales of variability in San Antonion Bay, Texas, Marine Ecology Progress Series, 1996 vol. 145 p. 245-268.
Sukenik et al. Regulation of Fatty Acid Composition by Irradiance Level in the *Eustigmatophyte Nannochloropsis* SP., J. Phycol., 1989, vol. 25, p. 656-692.
Broun et al., Catalytic plasticity of fatty acid modification enzymes underlying chemical diversity of plant lipids. Science, 1998, vol. 282; 1315-1317.
Kisselev L., Polypeptide release factors in prokaryotes and eukaryotes: same function, different structure. Structure, 2002, vol. 10: 8-9.
Wishart et al., A single mutation converts a novel phosphotyrosine binding domain into a dual-specificity phosphatase. J. Biol. Chem., 1995, vol. 270 (45): 26782-26785.
Whisstock et al., Prediction of protein function from protein sequence. Q. Rev. Biophysics., 2003, vol. 36 (3): 307-340.
Witkowski et al., Conversion of b-ketoacyl synthase to a Malonyl Decarboxylase by replacement of the active cysteine with glutamine. Biochemistry, 1999 vol. 38: 11643-11650.
Geng et al. "Construction of a System for the Stable Expression of Foreign Genes in *Dunaliella Salina*," Acta Botanica Sinica 46(3): 342-346 (2004).
Chen et al., "Highly Efficient Expression of Rabbit Neutrophil Peptide-1 gene in *Chlorella Ellipsoidea* Cells," Current Genetics 39(5-6): 365-370 (Jul. 2001).
Suga et al., "Control by Osmolarity and Electric Field Strength of Electro-Induced Gene Transfer and Protein Release in Fission Yeast Cells," Journal of Electrostatics 64(12): 796-801 (Nov. 2006).

\* cited by examiner

| Desaturase No. | SEQ ID NO | Desaturase Type | Times Up Regulated in Presence/Absence Nitrogen | Substrate 1 | Product 1 | Substrate 2 | Product 2 | Gene Regulation in Mutant Up/Down | Substrate 1 to Product 1 Conversion | Gene Regulation in Mutant Up/Down | Substrate 2 to Product 2 Conversion |
|---|---|---|---|---|---|---|---|---|---|---|---|
| 3 | 1 | Delta 12 Desaturase | 1.5X/Absence | Palmitoleic acid (16:2(n-7)) | 6,9,12-hexadecatrienoic acid (16:3(n-4)) | Oleic acid, cis-9-octadecenoic acid (18:1(n-9)) | Linoleic acid, all-cis-9, 12-octadecadienoic acid (18:2(n-6)) | Up | Increase product 1 by 85% | Up | Increase product 1 by 50% |
| 5 | 2 | Delta 12 Desaturase | Not Regulated | Oleic acid, cis-9-octadecenoic acid (18:1(n-9)) | 12-octadecadienoic acid (18:2(n-6)) | | | Down | Increase of substrate 1 by 100% | | |
| 7 | 3 | Omega 3 Desaturase | 4X/Presence | Arachidonic acid, all-cis-5,8,11,14-eicosatetraenoic acid (20:4(n-6)) | Eicosapentaenoic acid, all-cis-5,8,11,14,17-eicosapentaenoic acid (20:5(n-3)) | Linoleic acid, all-cis-9, 12-octadecadienoic acid (18:2(n-6)) | α-Linolenic acid, all-cis-9,12,15-octadecatrienoic acid (18:3(n-3)) | Up | Decrease of substrate 1 by 60%, EPA:ARA ratio changes from 7.5 to 22; a ~200% increase | Up | Increase of product 2 by 650%; 18:3n3 to 18:2n6 ratio changes from 2.5 to 15.8 (550% increase) |
| 9 | 4 | Delta 9 Desaturase | 6.6X/Absence | Palmitic acid, or hexadecanoic acid (16:0) | Palmitoleic acid, cis-9-hexadecenoic acid (16:1(n-7)) | | | Up | Increase of product 1 by 25%; increase of 16:1n7 to 16:0 ratio from 0.48 to 0.6; a 25% increase | | |
| 10 | 5 | Delta 9 Desaturase | 5X/Absence | Palmitic acid, or hexadecanoic acid (16:0) | Palmitoleic acid, cis-9-hexadecenoic acid (16:1(n-7)) | | | Up | Increase of product 1 by 34%; increase of 16:1n7 to 16:0 ratio from 1.02 to 1.19; a 16% increase | | |

FIG. 1

```
ATGGGACGCGGTGGCGAGCGGGTCGAGACGACGGAGTCTTTGAGCTTCACGGCCGACAAGGCGGGACCATCAAGCAGCGTGGGGGAAGATCACATGGG
ATGAGGTATGTGACGGGGCATGGCGAGGCGTCGGAGGAGAATGCAGGGAGGAAAGAGAGGGAGAAAGAAGGAAAGCAAGGTGTATCTGTGGCGGT
AGATTTGCCATCTATATGATCCTTTGAGTGCAGTGCTTGGAAGGCGTCAGTGCAATGTGAAGCGTGTATGATGACGGAAGCAGACACCTTCCCTTCCCTA
ATCTCTGTCCCTACAACCCCGCGTATCCTCTTCCGATCACCCACGCTCACACACACTCTATTTACTCTCCAGTGCTTCAGCACAAGACGCCTCAGGAGCTT
GGCTCGTGTATAGGAATAAGTCTACGACGTGTCGCAGATGTCACCCCGGGGGAACGTCATCTTCACTCACCGCGGGACTGCACGGATATTT
TCGCGGCGTTCCACCCTCTTGGCGCCACCTCTATCTTGATCCATTTTACATTGGCGAGCTGCGGACAAGAAGCCCGCAGGCAGGCGAACTTT
GAGCGGGCCTACAGGGATCTCAGGGGGAAGCTTATCGCGGGTGGGTTTTTCAAGGCGAAGGTCTTTGTACTATGTCTGGAAGGTAGTATCGACAGTTGCCTTG
CTGTAGGTGCGTGGAATGCTGGCTTGGTGCAGAACCTGGTGTTGGGTGACCTGGCCGGACATGTCGCCGGCAATGTTGCGCAGGTTTCTCGTGCATGGTGAA
CCATGACTTCCTGCACCACCAGGTATTTAAGAACCGTGCGTGCCAATGTCGAGAACCTGTATATCTGACATTGACACCTATCCCCATATACTGCCTG
AGAACAAGCATAACACTCACCACGCGGTGCCAACTCGTCGAGTCCTCCGAACGCGAAGACCCTGCTATACTCCCATCGCTGCTGTGCGAGGATTT
GTCGCTCAAGATGGCCGACAGGGCAGCAATACTAGGAGCATCAGCTTTGTCAGGCAGTCGTTGCGGCAACAAGGGCGAGCGGTGAGAGACAGGCGATCAAGATGT
CATGGTTGATGCAGTGCGTCGTTGTTGCTTGTCAGCGGCCCTGGAGCGAGTCTGTGGGAACAAGGGCGTGCGCGGATCAGGTCCTGTACTTCCTGGCGAGC
CGGGTTGGAGAAGGTGCGGGTTCTGTCGCGCTTGTTTCGGGCTGTTTCGGGCTGTTTCGGGCATGTACGGTGGCACAACGGCATGCTGTTACGACGCGGACGCCGCCGGCCGCCGGCCGACTTCTGGAAGCTGCAGG
CAGATGATGTGCGCGGAACGTGACGGGCTCGTGGTTGGTGCAGGGTTTCTGCAAGGATCACGGGGTGAAGTACCACGAGACGAATATGTGGAGGGACCAAGAGAGGTTG
TGACGACGAGGAACGTGACGGGCTACGACGCTTGTGGCGGCCTACCACCACCTGTTCCCATGATGATCCCGGCACGGC
ACGGCCTAGGGAAGCTCACGGGCTCGTGGAGGGTTTCTGCAAGGATCACGGGGTGAAGTACCACGAGACGAATATGTGGAGGGACCAAGAGAGGTTG
GCTCACTTGACGAGTGTGACGAAAGAGTTCGTGGCCGATTTCCCCGCCATGTAA
```

FIG. 2

ATGGGACGGCGGCGGTGAGAAGACGGTGACCCCTCTTCGCAAAAAACCCTCCTGATGCCGCTTCCACGATCAGCGGCACAGTCAGCGACCAAGCAAGGC
AGTAGAGGCCCTGCCACGGAGGAGGAGTCGCCAGGAGCCGTAAGAAGGCCGCACAATACGGTATCAACACTTCGGTCGACCGCGAAACACTGCTGAAGGGAGCTGGTAA
GTGCTTGTGATCGCTTGAGGGGTGATGGGTAAAAAACAGTTCCCTCCCATTCGTGCATGTGGTCAGACGGATATAAGAATTACGTGCCCTGACA
TTTGATGTCACCGCGCTGTCTTCACTTCCCGCTCCAATAGTATTATGTACGTGGACTGGGCGCTGCTGCCCCTTGTCCTTTTTCTTCCCTCCCTTGCATG
CCACTTAAGCATACCTCGCTCATTCACTTCCGCATGTCATCATAACCACAGGCTCCCTACTGCTCTTGAGCGTTCCCTCCTCTCCACTTGACCATCGACT
CCTTGCCCCTCCTCCTTCACCCTCCGACATCAAGAAGCGTGTTCCCGTACTGCTTTGAGCGTTCCCTCCTCTCCACTTGACCATCGACT
TGATCAAGTCGCTGTCCTCGGTACCTGCCTCATTACTGGGCACTTGCCTCCGAGTCCCGACCTCCGAGCGTCGTTATATTCTATGGCCGTTGTACTGGTACGCGC
AAGGCTGTGTGCTGACGGAGTGTGGCTCATGCCCAGAGTGCGGGCACCAATCGTTTCGCCTTACGAGAGCGTGAACAACTTCTTTGGGTGGCTCTT
GCACTCGGCCTTGCTTGTGCCCTATCACTCTTGGAGGATTTCCCATGGAAAGCACACACGGGGAGCTGCGAGAATGACGAGGTCTTTGCGCCG
CCTATTAAGGAGGAACTGATGGACGAGATTTGCTTCACTCCCTTTGGCGAATCTGTGCAGATAATCATAATGCGGCTTGTTTTCTCCGAAGGACGTCTGGA
ACTGCTCCTGAACGCTACGGGCCTAGGGCACATTGGTTTCGTGCTTGGCCTTGGCGTGCGTGGTATATGCCTGTGTGCAGTTTGGATTTCAAACGGTGGAAAGTATTACCTGCTGC
CATTATTGGTCCGACATTGGTTTCAATTCACCTGGTCCTCATCACGTACCTGCAGCACAGGACGTCTTCATCCCCACTTTCGGGGAGCGAGTGGACGTGGTTAG
CGTACATGGTGGTCAATTATCACCTGGTCCTCATCACGTACCTGCAGCACAGGACGTCTTCATCCCCACTTTCGGGGAGCGAGTGGACGTGGTTAG
GGCGCGCCCTTGCACGGTCGACCGATCCTTCGGCTGGCTTTGGACCATACGTTTCACCATATCAGTGACACTCAGTGACACTCTTCAGCAAGA
TGCCGTTTCTACCACGCCGGAGGCGAGTGGAGCACATTCGCAAGGCGTTGGGGACTATTATTTGAAGGATGATACCCCGATTGGAAGGCATTGTGGC
GAAGTTATACCCTGTGCAAGTACGTGGACTGCAAGTACGTGGACTCGAGGAGACGACGTATTCTACAAGCAGCGGGCATAG

FIG. 3

ATGGTTGAGCAAACGTTACCGACCTTGTCCCAGATCAAGAAAGCCATCCCCGAGAAATGCTTCCAGTACAACGCGGAGGGGG
TGGAGGGGGGAGTGGAGTGAAGCAGGGGGAGTGAAGGACAGGGGGAGAACGGGGTGATAAAGAGGGATAGGTTGAGAGAGGGAA
AAGGGAAGAAGTGTTGCAAGGACGTGGTGTTGCAGAAGGACGTGGTGTACCTGTGCGTGCCATTCCTCCTGTCTCCATTCCCCTTCAGAAATCCTCCGCT
AGCAGTCCGAAGCGTTGTCACCCTTCGCGGCCTTGGCGGCCTTGGCGGCACTCTACTTTGTTATCCACAGTGCAGGCCAAGTATGGATTGCC
CCTTTACTACATGCTGAGGACTTCGCGCGATCTGAGGGCCTTGGCGGCACTCTACTTTGTTATCCACAGTGCAGGCCAAGTATGGATTGCC
TGGTTTGGTTTGTGTGGTGGAACCTCGCAGGTAGGGAGGGATGGAAGGAAGAGAATTGGGGAAAGCCATGAGC
CGTCTTATACGTCTTCTAGGCACTCACAAACTCTTCTCCCCCGAGTAGGCTCCCCAGGCTTTCATGTGGTGCTCTTCG
TGATAGGCCACGATTGCGGCCATGGCCTCCTTCTCCGAGTACAAGTGGCTCAATGACATATGCGGTCACATTGCACGCCCCCTT
GATGGTGCTTACTGGCCTTGGGCAGAAGGTATGGGAGCCAGGCGCCCCCTCCCCTCCCTCCCCTACTCCCTCCCTGCCAGTCCCACGCTT
GACATGTGCGATCATCTCATTCATTCTCTCTGCGGCCTCATCCATCCCCTCCCTCCCCCTCCTTTGCCAGTCCCACGCTT
CACCACAGTGACCACACCAACCACTGACTAAGGACACATGTCACACCCGTGGATGACCAAGGAGGTGTCACGCCTTCACGCCTTCCTC
GAGGGCGATATGTGTGGGATGAACGCTATAGAGAAGGCACGGCTGTTTGATCCTGTGGCATACCTCACGCCTTCCTC
CTCCCCTCCCTCCCTCCTCCCTTTTCAGGAGCTTGACCCCATTGAGACGGCGTTGCTGAGAAACCCGCTGTCCTCTCATCA
AGTACACCTCCTTTACTCTTTGCGGGCAAGATGGATGCCAGTAGGAGGGATAGGGGACGGATGAGGGAGA
GGACGGGAAGTCGGACACGGAGTGGGCTCGTTCTTGTCCACTCTGATTGCTCACCTCCCTCCCTCCTCCCTCC
CTCCCTCCCTTCCGTCTGGACACAGCAGCCATGTAGTTCCATTCTCCCCCTCGGGCTGTACATCGGGCTCGAGGGCTGCAATGCGCTGT
GTCGACGCTGGGTATGGTCGTCGCAGGCGCCTTTGTGTACATGCTGGATCGTGGAAGGAGGGATGGCGAGGAT
AGGATCCATTTATGTGGTGCCGTTGCTGTTCAATGCTGGAGTGGAGCATGGCGAGCATGGACAGCACGAAGGCATGGGGATTGAC
CAAGGTTTATCATTGGTTAAATATATGTGACAACTCTAATTAATTGATTACTTCATGTTTAATTGACAATTCGTTCTGGTG
ATGGTGAAGACCAAGTGACAGTTTCCACAGTTGTCTTAGCTCAAGATAAGCTGGCCTCTTTCCTCCGCCCTCCT
TCCCTTAGACCTCTCCCACATATCACGGATGGCCACGTGGCGCACCACGTCTTCTTCACGACAGATCCGACTACCACCTGACG
GCGGCCACGGCCGCTGTGACCGTTAACTACCGTTTGAAATACGTCGCGGGCCAGGGCGTGCAACTACGGGGGACCTACAGAAGAGGAGCTGGAATTTCTCGCTCGTTT
CACGGAGCTTAACTACCGTTTGAAATACGTCGCGGGCCAGGGCGTGCAACTACGGGGGACCTACAGAAGAGGAGCTGGAATTTCTCGCTCGTTT
AGAGCGAAGGAGTGAGGGAAAGAGTGAGGAAAAGTAAATATAGATGGAGGGTTTGCAGCTCAGCTTTCTTCTTCTTCACCCT
TGCTCCCCTGCTCTGTAACCATACACAGTCGCTCGCAAGACCCTGCTTCGCGCGTGCCGTGCCGTGCCTGCGTCCCTCTCTCTCTCTCCTC
TTCCTCCCTCGCCAGAGCGTCGTGTCAAGGCGGCTGTGTCCGGTGTGCCGTGCGTGCCTGCGTCCCGAGAAGGAAG
ACCAACACGCAAGGCGCTCTCCCACCCGTTCATCCTCCCTCCGTAA

FIG. 4

ATGCACGTCTACCCGACAAGCACGAAGTCATTGTCAGCATGGAGCCCATGGTGGAAGGGATGTCTCCTCCCCACGGGGAGAAGCTT
GGCAACCGTCCGACTTTGTCCCGGACATGGTGGGGGACATGGTGGTACAAGGAAGGGTGGGACAAGGAGGTAAAGGAATTCAGGGAAGACGAGGTTGCCGACGAGACG
CTGGTGGTCTTGTGGGGGGACATGGTGGTACTGAGGAGGCGTTGCCCACTTACCAGACGCGTTGTTGAACACGTTCGAGGGCGTGGATGACCCACCGGACG
AGTCCTTCGGCCTGGTGCCGATGGACACGGGGGTGGACGAGCGAGGGGAACAGGCACGGGGATCTGCTCAACGTGTACTTGACGGGCGT
GGACATGCGCGCGATCGAGTGCACGATTCAGCACCTGGTACGTGGGGATGGGGAGGGAGGGAGGGAGGGATGGAGGAAGGCTCTGTTCTTGTGT
TCCCCCCTTCGTCTCGCGCGATGTCTAACTCATTCTTCCACCCTCCCTGGTCTCGTAAATTAGATTTCGAGCGGTTCAACCCCAAATCAAGAAG
GATCCGTACAAGGGTTTCGTATACACCTCCTTCAAGAGCGAGCAACCAAGATCTCCATCAGAATGTGGCGGCCAACAGCGCGGTGATGGCA
ATCTGGTCTGATCTGCAGTAAGATTGCAGGGGATGAGTCGAGGCACGAGAAGGCATACCAAGCCATCTTCCAGGAGATCCTCAAGAAGGACCCGGAAG
GGGGGTTGAAGAGCTTCTATGAGTTAATGAGTCAGTCAGGTAGGAGGCGGAGAGAGAGGGAGGGAGGGGAGGTAGTACGCATTAGGAG
GCAGGAGGAAGGGAACGACACAAGTACTTTCACCATGGGCCAAGATACGGCTGTTTACCTTTCCCTCGCTCTCGCTCTCCTCTCCCTCC
CTCATCTCAGATCACCATGCTGCCGTGATGACGGACGCCACGACCGGACACTTCTGAGACATCTTCGTCACGGCCGAGAAGCTCGGTGTCTACA
CGGCAGTGGACTACGCCAACATTCTGGAATATTTGGTGAGACATGGGAGACATGGGAGCACATGGAGACACAGGAGGCCTGTCTTCTGAAGGGCCAAGTACAGGAGA
AGCTCTGCAAGCTCGCGCCCCGATACATGAGGCTTGCCGAGATGGAGTCTTGAGTCTTGACCGGGTGAAAAGATGCCCAAGGACGCCTATTCTGGATCATGGACG
CGTGGCTTAA

FIG. 5

ATGGTCTTCCAGCTCGCCCGAGACTCTGTCTCGGCCCTGGTCTATCATTCAAAGAAGGAAACCTTAACTGGCCTATGATTATCTACCTCGTC
CTTGTCCACTTGGGCGGGCTACATCGGTCTGACTACCATTCTGGCTTGCAAATGGCAAACTCTCTGGAAGCGTTCATCCTATGGCCCATCACC
GGGCTGGGGATTACTGCCGGGCTACACGACTTTGGGCACACCGTTCGTACAACGCCTTATCGCATCCGTTGCCTATCGCATCCGTTGTTCAA
CTCAATTGCGAACCAAGGCAGCATCTACCACTGGTCCGGACCACCGCGTGACCACAAGTACTCCGAGACTGATGCTGACCACATAAC
GCCACCCGTGGCTCTTCTTCGCGCACATGGGCTGGCTCATTGTTAAGAAGCACCCCAAGGTCGTGAAGGGGAAGCAACTCGATTCT
CCGATTTGGCTGCCGATCCCGTGGTCGCAGCTGTCCAGCGTTTGGGTGAGGCGTTCTGAAGCGTCTGATATGTTGGTGCTGACTCACCTGGATGG
GCATCGAGGTTCTGGGGTGAGGCGTTCTGAAGCGTCTGATATGTTGGTGCTGACTCACCTGGATGG
TAACAGTGCGGGCCACTTGTATGGCGACCACCGTACGACCCTACCATGTGGCCGGCGAGAACCCGTTGGTATCGGTAGTGGCGATCGG
AGAAGGCTGGCATAACTGCCACCATCGTTACCCTACGACTACGTTACCCTACCTTCAACCGACCGAGTTTGGGATTTGGGCAGTTCAACCGACCAAGGCG
TCATTGATTTTTTGCGCCATAGGGATGGTGACGAACGAAAACGTGCGAAACCGTGCGAAAGTCAAGGAATCAAGGCAAGG
GATGCGGCGAATGGAAGAGCATGAAAGATTCAAGGGGCGCAACAACCAGGGTGGGAGGAGCAATCACCCAAGTACAACTAA

FIG. 6

MVRQHKTPQDAWLVYRNKVVYDVSGWQDHPGGNVIFTHAGGDCTDIFAAFHPLGATSYLDPFYIGELEPGSDKPAAQANFERAVRDLRGKLIAGGF
FKANPLYYVWKVVSTVALAVGAWMLVAWSQNLGVQMLSAFLVALFWQQCGWLAHDFLHHQVFKNRALGDLAGIVIGNVFQGFSVAWWNKH
NTHHAVPNLVESSPDAQDGDPDIDTMPILAWSLKMADRAQQYSWGPFFVRHQSLLYFPILLVARISWLMQSFLVFDSVPGASLWATKGATAERQA
IKNVGLEKVGLVAHYLWYGALMLCHMSLARALLYFLASQMMCGFLLALVFGLGHNGMAVYDADARPDFWKLQVTTTRNVTGSWLVQWFCGGLG
YQVDHHLFPMIPRHRLGKLHGLVEGFCKDHGVKYHETNMWEGTKEVLAHLSSVTKEFVADFPAM

FIG. 7

MGRGGEKTVTPLRKKTLLDAASTISGTVRPSKAVEALPTEELRKKAAQYGINTSVDRETLRELAPYGDILLRNDAPKSLPLAPPPFTLSDIKNAVPRHCFERSLST
SLFHLTIDLIQVAVLGYLASLLGHSDVPPMSRYILWPLYWYAQGSVLTGVWVIAHECGHQSFSPYESVNNFFGWLLHSALLVPYHSWRISHGKHHNNTGSCE
NDEVFAPPIKEELMDEILLHSPLANLVQIIMLTIGWMPGYLLLNATGPRKYKGLSNSHFNPNSALFSPKDRLDIIWSDIGFFVALACVVYACVQFGFQTVGKYY
LLPYMVVNYHLVLITYLQHTDVFIPHFRGSEWTWFRGALCTVDRSFGWLLDHTFHHISDTHVCHHIFSKMPFYHAQEASEHIRKALGDYYLKDDTPIWKALW
RSYTLCKYVDSEETTVFYKQRA

FIG. 8

MVEQTLPTLSQIKKAIPEKCFQKSLLRSFYMLRDFAALAALYFVPTVQAKYGLPGLFVWWNLAGFMWCLFVIGHDCGHGSFSEYKWLNDICGHICHAPLM
VPYWPWQKSHRLHHMYHNHLTKDMSHPWMTKEVFEDLTPFEQALLENPLSLFIKYTFLYLFAGKMDGSHVVPFSPLFTDTKERVQCAVSTLGMVVAGALVYI
GLEGGKEGGMARIGSIYVVPLLVFNAWITMVTYLQHHDEDTKVVAEGEWNYIKGALETIDREYGMGIDDLSHNITDGHVAHHLFFTQIPHYHLTAATAAVRQC
LQPTGTYKKRRSWNFLARFTELNYRLKYVAGQGVLSYDVEVARKTPASAVTSSFSSSSSSLPAEAAVKAAAAVPVAAVAAPVREGRPTRKRSPTRSSPP

FIG. 9

MHVYPDKHEVIVSMEPMVEGMLSKLLPTGEKAWQPSDFVPDLTKEGWEDEVKEFREKAETLPDETLVVLVGDMVTEEALPTYQTLLNTFEGVDDP
TGTSPSAWCRWTRGWTSEENRHGDLLNRYLYLTGRVDMRAIECTIQHLISSGFNPKIKKDPYKGFVYTSFQERATKISHQNVARLANSAGDGNLGLICS
KIAGDESRHEKAYQAIFQEILKKDPEGGLKSFYELMSDQITMPAVMMTDGHDPDLFEHFSVTAQKLGVYTAVDYANILEYLVETWDIEHMGGLSSEGA
KYQEKLCKLAPRYMRLAEMSLDRVKKMPKTPYSWIHGRVA

FIG. 10

MVFQLARDSVSALVYHFKEGNLNWPMIIYLVLVHLAGYIGLTTILACKWQTLLEAFILWPITGLGITAGVHRLWAHRSYNATLPYRILLMLFNSIANQGSIY
HWSRDHRVHHKYSETDADPHNATRGFFFAHMGWLIVKKHPKVVEGGKQLDFSDLAADPVVRFQRDWDPWFAQFMCFVMPALVASRFWGEAFWN
AFWVAGALRYMLVLHFTWMVNSAAHLYGDHPYDPTMWPAENPLVSVVAIGEGWHNWHHRYPYDYAASEFGISQQFNPTKAFIDFFAAIGMVTNRK
RATGAWAKLKESRARDAANGKSMKDFKGRGSGSDYGTTNTNYAVSNKTVVTDKGAQQPGWEESNHPKYN

ALGAL DESATURASES

CROSS-REFERENCE TO RELATED APPLICATIONS

The present application claims the benefit and priority of U.S. Provisional Patent Application Ser. No. 61/480,353 filed on Apr. 28, 2011, titled "Desaturases," which is hereby incorporated by reference.

The present application is related to U.S. Non-Provisional patent application Ser. No. 12/581,812 filed on Oct. 19, 2009, titled "Homologous Recombination in an Algal Nuclear Genome," which is hereby incorporated by reference.

The present application is related to U.S. Non-Provisional patent application Ser. No. 12/480,635 filed on Jun. 8, 2009, titled "VCP-Based Vectors for Algal Cell Transformation," which is hereby incorporated by reference.

The present application is related to U.S. Non-Provisional patent application Ser. No. 12/480,611 filed on Jun. 8, 2009, titled "Transformation of Algal Cells," which is hereby incorporated by reference.

REFERENCE TO SEQUENCE LISTINGS

The present application is filed with sequence listing(s) attached hereto and incorporated by reference.

BACKGROUND OF THE INVENTION

Field of the Invention

This invention relates to molecular biology, and more specifically, to algal desaturases.

SUMMARY OF THE INVENTION

Isolated nucleotide sequences encoding polypeptides having desaturase activity, which utilize fatty acids as substrates.

BRIEF DESCRIPTION OF THE DRAWINGS

FIG. 1 is a table of exemplary desaturases.
FIG. 2 illustrates the nucleotide sequence encoding desaturase 3 (SEQ ID NO:1).
FIG. 3 illustrates the nucleotide sequence encoding desaturase 5 (SEQ ID NO:2).
FIG. 4 illustrates the nucleotide sequence encoding desaturase 7 (SEQ ID NO:3).
FIG. 5 illustrates the nucleotide sequence encoding desaturase 9 (SEQ ID NO:4).
FIG. 6 illustrates the nucleotide sequence encoding desaturase 10 (SEQ ID NO:5).
FIG. 7 illustrates the amino acid sequence encoded by desaturase 3 (SEQ ID NO:6).
FIG. 8 illustrates the amino acid sequence encoded by desaturase 5 (SEQ ID NO:7).
FIG. 9 illustrates the amino acid sequence encoded by desaturase 7 (SEQ ID NO:8).
FIG. 10 illustrates the amino acid sequence encoded by desaturase 9 (SEQ ID NO:9).
FIG. 11 illustrates the amino acid sequence encoded by desaturase 10 (SEQ ID NO:10).

DETAILED DESCRIPTION OF THE INVENTION

A fatty acid is a carboxylic acid with a long aliphatic tail (chain), which is either saturated or unsaturated. Saturated fatty acids are long-chain carboxylic acids that usually have between 12 and 24 carbon atoms and have no double bonds. Unsaturated fatty acids have one or more double bonds between carbon atoms. Most naturally occurring fatty acids have a chain of an even number of carbon atoms, from 4 to 28. A fatty acid desaturase is an enzyme that removes two hydrogen atoms from a fatty acid, creating a carbon/carbon double bond. These desaturases are classified as either Delta desaturases, indicating that the double bond is created at a fixed position from the carboxyl group of a fatty acid (for example, a delta nine ("Δ9") desaturase creates a double bond at the 9th position from the carboxyl end) or classified as Omega desaturases (for example, an omega three ("ω3") desaturase, which creates the double bond between the third and fourth carbon from the methyl end of the fatty acid).

Provided herein are isolated nucleotide sequences encoding polypeptides having desaturase activity, which utilize fatty acids as substrates.

The inventors sequenced the entire genome of algal genus *Nannochloropsis* and identified genes involved in fatty acid metabolism. They identified various desaturases, including exemplary desaturases which they designated as desaturase 3 ("desat3"), desaturase 5 ("desat5"), desaturase 7 ("desat7"), desaturase 9 ("desat9"), and desaturase 10 ("desat10").

The inventors manipulated the activities of the above-specified exemplary desaturase genes by:

1. Overexpression of the subject desaturase gene with a strong promoter.
2. Promoter replacement or promoter insertion in front of the subject desaturase gene within the genome via homologous recombination.
3. Knock out of the subject desaturase gene via insertion of a transformation construct into the gene or replacement of a part of or the entire subject desaturase gene via homologous recombination.

Exemplary support for the above-mentioned methods may be found in U.S. Non-Provisional patent application Ser. No. 12/581,812 filed on Oct. 19, 2009, titled "Homologous Recombination in an Algal Nuclear Genome," U.S. Non-Provisional patent application Ser. No. 12/480,635 filed on Jun. 8, 2009, titled "VCP-Based Vectors for Algal Cell Transformation," and U.S. Non-Provisional patent application Ser. No. 12/480,611 filed on Jun. 8, 2009, titled "Transformation of Algal Cells," all of which are hereby incorporated by reference.

Accordingly, the inventors were able to manipulate the activities of the various exemplary desaturases for the purpose of modifying the contents of certain fatty acids within algal genus *Nannochloropsis*.

FIG. 1 is a table of exemplary desaturases. The table includes the number of the respective desaturase, captioned "Desaturase No.", the corresponding sequence identifier number, captioned "SEQ ID NO", the type of desaturase, captioned "Desaturase Type", the relative increase in desaturase gene regulation with respect to the presence or absence of Nitrogen, captioned "Times Up Regulated in the Presence/Absence of Nitrogen", a first desaturase substrate, captioned "Substrate 1", the resulting first product, captioned "Product 1", a second desaturase substrate (if applicable), captioned "Substrate 2", the resulting second product (if applicable), captioned "Product 2", whether the desaturase gene was up-regulated or down-regulated in a particular mutant construct (with respect to the Substrate 1 to Product 1 reaction), captioned "Gene Regulation in Mutant Up/Down", the observed increase or decrease of the corresponding substrate to product reaction by a mutant construct (as compared to a wild-type *Nannochloropsis* control cell), captioned "Substrate 1 to Product 1 Conversion" whether the desaturase gene was up-regulated or down-regulated in a particular mutant construct (with respect to the Substrate 2 to Product 2 reaction) (if applicable), captioned "Gene Regulation in Mutant Up/Down" and the observed increase or decrease of the corresponding substrate to product reaction by a mutant construct (as compared to a wild-type *Nannochloropsis* control cell), captioned "Substrate 2 to Product 2 Conversion" (if applicable).

As shown in FIG. 1, the inventors identified five exemplary desaturases, designated as desaturase 3 ("desat3"), desaturase 5 ("desat5"), desaturase 7 ("desat7"), desaturase 9 ("desat9"), and desaturase 10 ("desat10"). Each desaturase has a corresponding SEQ ID NO, reflecting a nucleotide sequence for the respective desaturase. The desaturase type (which indicates corresponding enzymatic activity) is also shown in FIG. 1. The column captioned "Times Up Regulated in the Presence/Absence of Nitrogen" reflects whole transcriptome comparisons of samples grown under Nitrogen sufficient ("N+") or Nitrogen deficient conditions ("N−"). The columns captioned "Substrate 1 to Product 1 Conversion" and "Substrate 2 to Product 2 Conversion" (if applicable) show the observed increase or decrease of the corresponding substrate to product reactions by a mutant construct (as compared to a wild-type *Nannochloropsis* control cell).

Referring again to the table in FIG. 1, desaturase 3, a Delta 12 desaturase, is approximately 1.5 times up-regulated in the absence of Nitrogen. Desaturase 3 increases the conversion of Palmitolenic acid (16:2(n-7)) to 6,9,12-hexadecatrienoic acid (16:3(n-4)) by approximately 85% (when compared to a wild-type *Nannochloropsis* control cell). Desaturase 3 also increases the conversion of Oleic acid, cis-9-octadecenoic acid (18:1(n-9)) to Linoleic acid, all-cis-9, 12-octadecadienoic acid (18:2(n-6)) by approximately 50% (when compared to a wild-type *Nannochloropsis* control cell).

Desaturase 5, as shown in the table in FIG. 1, is also a Delta 12 desaturase. Desaturase 5 is not regulated in the presence or absence of Nitrogen. Desaturase 5 decreases the conversion of Oleic acid, cis-9-octadecenoic acid (18:1(n-9)) to 12-octadecadienoic acid (18:2(n-6)) by approximately 100% (when compared to a wild-type *Nannochloropsis* control cell).

Desaturase 7, shown in the table in FIG. 1, is an Omega 3 desaturase. Desaturase 7 is approximately 4.0 times up-regulated in the presence of Nitrogen. Overexpression of Desaturase 7 decreases the amount of Arachidonic acid, all-cis-5,8,11,14-eicosatetraenoic acid (20:4(n-6)) ("ARA") by approximately 60% due to more conversion of ARA to Eicosapentaenoic acid, all-cis-5,8,11,14,17-eicosapentaenoic acid (20:5(n-3)) ("EPA") (when compared to a wild-type *Nannochloropsis* control cell). In fact, the EPA to ARA ratio changes from about 7.5 to about 22, an approximate 200% increase. Desaturase 7 increases the conversion of Linoleic acid, all-cis-9, 12-octadecadienoic acid (18:2(n-6)) to a-Linolenic acid, all-cis-9,12,15-octadecatrienoic acid (18:3(n-3)) by approximately 650% (when compared to a wild-type *Nannochloropsis* control cell). In fact, the ratio of a-Linolenic acid, all-cis-9,12,15-octadecatrienoic acid (18:3(n-3)) to Linoleic acid, all-cis-9, 12-octadecadienoic acid (18:2(n-6)) changes from approximately 2.5 to approximately 15.8, an approximate 550% increase.

Desaturase 9, shown in the table in FIG. 1, is a Delta 9 desaturase. Desaturase 9 is approximately 6.6 times up-regulated in the absence of Nitrogen. Desaturase 9 increases the conversion of Palmitic acid, or hexadecanoic acid (16:0) to Palmitoleic acid, cis-9-hexadecenoic acid (16:1(n-7)) by approximately 25%, while increasing the ratio of Palmitoleic acid, cis-9-hexadecenoic acid (16:1(n-7)) to Palmitic acid, or hexadecanoic acid (16:0) from about 0.48 to 0.6, an approximate increase of 25%.

Desaturase 10, shown in the table in FIG. 1, is a Delta 9 desaturase. Desaturase 9 is approximately 5.0 times up-regulated in the absence of Nitrogen. Desaturase 9 increases the conversion of Palmitic acid, or hexadecanoic acid (16:0) to Palmitoleic acid, cis-9-hexadecenoic acid (16:1(n-7)) by approximately 34%, while increasing the ratio of Palmitoleic acid, cis-9-hexadecenoic acid (16:1(n-7)) to Palmitic acid, or hexadecanoic acid (16:0) from about 1.02 to 1.19, an approximate increase of 16%.

FIG. 2 illustrates the nucleotide sequence encoding desaturase 3 (SEQ ID NO:1).

The inventors found that desaturase 3 is slightly up-regulated under Nitrogen starvation. The inventors prepared a construct utilizing desaturase 3 that included a strong upstream promoter. This resulted in expression of elevated amounts of 16:3n4 and 18:2n6 fatty acids.

FIG. 3 illustrates the nucleotide sequence encoding desaturase 5 (SEQ ID NO:2).

The inventors found that desaturase 5 encodes a fatty acid desaturase with high homology to Delta 12 desaturases. The inventors also found that overexpression of this desaturase gene under the control of an inducible Urease promoter leads to higher expression levels of 18:1n9 fatty acids and poly unsaturated fatty acids ("PUFAs") with 18 or more carbon atoms, when the constructs are grown under Nitrogen starvation conditions (please note: the promoter is induced under Nitrogen starvation).

In other experiments, the inventors determined that the desaturation step at the Delta 12 position is likely a major bottleneck for channeling carbon into the PUFA biosynthesis pathway. While 18:1n9 fatty acids are steadily increasing during Nitrogen starvation, 18:2n6 fatty acids (derived from the Delta 12 desaturation of said 18:1n9 fatty acids) are decreasing (on a percent basis of all fatty acids), as are all fatty acids in the pathway leading to the production of Eicosapentaenoic acid ("EPA"). The inventors concluded that the desaturase 5 gene increases carbon flux into the PUFA biosynthesis pathway during Nitrogen starvation if the desaturase 5 gene is over-expressed.

FIG. 4 illustrates the nucleotide sequence encoding desaturase 7 (SEQ ID NO:3).

The inventors prepared various constructs (promoter replacements, knock-outs, and over expression constructs) and found that down-regulation of the desaturase 7 gene results in a lower EPA/Arachidonic acid ("ARA") ratio, i.e. less ARA is desaturated to EPA. The inventors observed in mutant constructs that lower desaturase 7 transcription is due to an exchange of the native promoter in the wild-type *Nannochloropsis* cells. The inventors observed that the mutant constructs had nearly double the levels of ARA with less levels of EPA, when compared to the wild-type *Nannochloropsis* control cells.

The inventors also observed that up-regulation of the desaturase 7 gene results in higher 18:3n3/18:2n6 and EPA/ARA ratios, i.e. more 18:2n6 is converted to 18:3n3, and more ARA is converted into EPA. Accordingly, the inventors observed that the EPA/ARA ratio was nearly doubled.

FIG. 5 illustrates the nucleotide sequence encoding desaturase 9 (SEQ ID NO:4).

FIG. 6 illustrates the nucleotide sequence encoding desaturase 10 (SEQ ID NO:5).

The inventors observed that both desaturase 9 and desaturase 10 appear to be Delta 9 desaturases acting primarily on 16:0 fatty acids or on 16:0 fatty acids attached to other compounds. Promotor exchange studies, in which the inventors exchanged the native wild-type promoter of *Nannochloropsis* against a strong promoter, revealed an up-regulation of said activity under Nitrogen deficient conditions. Thus, under Nitrogen starvation, a high percentage of fatty acids are channeled to the accumulation of 16:1n7 fatty acids through the action of the desaturase 9 gene, meaning less fatty acids are entering the PUFA pathway. The inventors also replaced the promoters of the desaturase 9 genes with promoters of moderate strength and which are putatively not regulated when cells enter Nitrogen starvation, with the goal to avoid carbon flux into the biosynthesis of 16:1n7 and 18:1n7 fatty acids and to increase carbon flux into the PUFA biosynthesis pathway during starvation. The inventors found that these genes are excellent targets for over-expression, in order to achieve elevated PUFA biosynthesis. Down-regulation of these (or other) genes, as an example, by replacement of the endogenous promoter or insertion of a weaker promoter in front of the respective desaturase gene may lead to a higher content of short chain fatty acids. Down-regulation of transcription could also be achieved, in some cases, by insertion of a commonly strong promoter in front of the respective desaturase gene, presumably by modifying the respective chromatin arrangement around the desaturase gene, thus leading to a lower transcription level. Also, the introduction of point mutations into the desaturase gene when inserting another promoter in front of the desaturase gene via the homologous recombination flanks may lead to an altered activity of the respective gene products.

The inventors also observed an increase of 16:1n7 lipids in a selected desaturase 10 over expression mutant under nitrogen sufficient conditions, clearly demonstrating that there is an approximately 34% increase in 16:1n7 fatty acids in this mutant when compared to the wild-type *Nannochloropsis* cells during the same experiment.

FIG. 7 illustrates the amino acid sequence encoded by desaturase 3 (SEQ ID NO:6).

FIG. 8 illustrates the amino acid sequence encoded by desaturase 5 (SEQ ID NO:7).

FIG. 9 illustrates the amino acid sequence encoded by desaturase 7 (SEQ ID NO:8).

FIG. 10 illustrates the amino acid sequence encoded by desaturase 9 (SEQ ID NO:9).

FIG. 11 illustrates the amino acid sequence encoded by desaturase 10 (SEQ ID NO:10).

While various embodiments have been described above, it should be understood that they have been presented by way of example only, and not limitation. Thus, the breadth and scope of a preferred embodiment should not be limited by any of the above-described exemplary embodiments.

What is claimed is:

1. An isolated nucleotide sequence encoding a polypeptide having desaturase activity, the nucleotide sequence having at least 95% sequence identity to SEQ ID NO:3.

2. The isolated nucleotide sequence of claim 1 wherein the sequence encodes a functionally active desaturase which utilizes a fatty acid as a substrate.

3. The isolated nucleotide sequence of claim 2, wherein the functionally active desaturase comprises amino acids having the sequence set forth as SEQ ID NO:8 or a sequence at least 95% identical thereto.

4. An isolated nucleotide sequence encoding a polypeptide having desaturase activity, the nucleotide sequence having at least 95% sequence identity to SEQ ID NO:4.

5. The isolated nucleotide sequence of claim 4 wherein the sequence encodes a functionally active desaturase which utilizes a fatty acid as a substrate.

6. The isolated nucleotide sequence of claim 5, wherein the functionally active desaturase comprises amino acids having the sequence set forth as SEQ ID NO:9 or a sequence at least 95% identical thereto.

7. An isolated nucleotide sequence encoding a polypeptide having desaturase activity, the nucleotide sequence having at least 95% sequence identity to SEQ ID NO:5.

8. The isolated nucleotide sequence of claim 7 wherein the sequence encodes a functionally active desaturase which utilizes a fatty acid as a substrate.

9. The isolated nucleotide sequence of claim 8, wherein the functionally active desaturase comprises amino acids having the sequence set forth as SEQ ID NO:10 or a sequence at least 95% identical thereto.

10. The isolated nucleotide sequence of claim 1 wherein the sequence is derived from algae.

11. The isolated nucleotide sequence of claim 10 wherein the algae is of genus *Nannochloropsis*.

* * * * *

SEQUENCE LISTING

```
<160> NUMBER OF SEQ ID NOS: 10

<210> SEQ ID NO 1
<211> LENGTH: 1698
<212> TYPE: DNA
<213> ORGANISM: Nannochloropsis

<400> SEQUENCE: 1
atgggacgcg gtggcgagcg ggtcgagacg acggagtctt tgagcttcac ggccgacaag      60
gcggggacca tcaagcagcg tgggggggaag atcacatggg atgaggtatg tgacggggca     120
tggaggcgtc ggacggagga atgcagggag aaagggaaag agaggagaaa ggaaagcaag     180
gtgtatctgc tgtggcggta gatttgccat ctatatgatc ctttgagtgc agtgcttgga     240
tggaaggcgt cagtgcaatc ctgtatgtga tgacggagga agcagcacac cttcccttcc     300
ctaatctctg tccctacaa ccccgcgtat cctcttctcc cgatcaccca cgctcacaca     360
cacctattta ctctccaggt gcgtcagcac aagacgcctc aggacgcttg gctcgtgtat     420
aggaataagg tctacgacgt gtcgggctgg caagatcacc ccgggggggaa cgtcatcttc     480 actcacgccg gcggggactg cacggatatt ttcgcggcgt tccaccctct tggcgccacc     540
tcttatcttg atccatttta cattggcgag ctggagccgg gctcggacaa gaagcccgca     600
gcgcaggcga actttgagcg ggcctacagg gatctcaggg ggaagcttat cgcgggtggg     660
tttttcaagg cgaatccttt gtactatgtc tggaaggtag tatcgacagt tgcccttgct     720
gtaggtgcgt ggatgctggt ggcttggtcg cagaacctgg gcgtgcagat gctgtctgcg     780
tttttggtgg ctctgttctg gcagcaatgt ggctggttgg cccatgactt cctgcaccac     840
caggtattta agaaccgtgc gttgggtgac ctggccggca tcgttatcgg caatgtcttc     900
cagggtttct ccgtggcatg gtggaagaac aagcataaca ctcaccacgc ggtgcccaac     960
ctcgtcgagt cctctccgga cgcgcaagac ggagaccctg acattgacac catgcccata    1020
ctggcctggt cgctcaagat ggccgacagg gcgcagcaat actcatgggg acccttcttt    1080
```

```
gtcaggcatc agtcgctgct atacttcccc atcctgctcg tggcgcggat tcatggttg    1140 atgcagtcgt tcttgtttgt ctttgactcc gtccctggag cgagtctgtg ggcaaccaag   1200
ggcgcgacgg ctgagagaca ggcgatcaag aatgtcgggt tggagaaggt ggggctggtt   1260
gcgcactacc tgtggtacgg tgcgctgatg ctgtgccaca tgtccctggc ccgcgccctg   1320
ctgtacttcc tggcgagcca gatgatgtgc gggttcttgc tcgcgcttgt tttcgggctt   1380
gggcacaacg gcatggctgt ttacgacgcg gacgcccggc ccgacttctg gaagctgcag   1440
gtgacgacga cgaggaacgt gacgggctcg tggttggtgc agtggttctg tggcggcctc   1500
ggctaccagg tggaccacca cctgttcccc atgatcccgc ggcaccgcct agggaagctc   1560
cacgggctcg tggagggttt ctgcaaggat cacggggtga agtaccacga gacgaatatg   1620
tgggagggga ccaaagaggt gttggctcac ttgagcagtg tgacgaaaga gttcgtggcc   1680
gatttccccg ccatgtaa                                                 1698
```

<210> SEQ ID NO 2
<211> LENGTH: 1576
<212> TYPE: DNA
<213> ORGANISM: Nannochloropsis

<400> SEQUENCE: 2

```
atgggacgcg gcggtgagaa gacggtgacc cctcttcgca aaaaaccct cctggatgcc      60 gcttccacga tcagcggcac agtcagacca agcaaggcag tagaggccct gcccacggag    120
gagctgcgta agaaggccgc acaatacggt atcaacactt cggtcgaccg cgaaacactg    180
ctgagggagc tggtaagtgc ttgtgatcgc ttgaggggtg gatgggtaaa aacagttccc    240
tcccattcgt gcatgtggtc agacggatat aagaattacg tgccatgccc ttgacatttt    300
gatgtcaccg cgctgtcttc acttcccgct ccaatagcta ttatgtacgt ggactggcgg    360
ctgctgcccc ttgtcctttt ttcttccctc ccttgcatgc cacctaagca tacctcgctc    420
attcactttc cgcatgtcat cataaccaca ggctccctac ggcgatatcc tcctccgcaa    480
tgacgcccct aaatccctgc cccttgcccc tcctcctttc accctctccg acatcaagaa    540
cgctgttccc cgtcactgct tgagcgttc cctctccacc tccctcttcc acttgaccat    600
cgacttgatc caagtcgctg tcctcgggta ccttgcctca ttactgggcc actccgacgt    660
cccgcccatg tctcgttata ttctatggcc gttgtactgg tacgcgcaag gctctgtgct    720
gacgggagtg tgggtcattg cccacgagtg cgggcaccaa tcgttttcgc cttacgagag    780
cgtgaacaac ttctttgggt ggctcttgca ctcggcttg cttgtgccct atcactcttg    840
gaggatttcc catggaaagc accacaacaa cacggggagc tgcgagaatg acgaggtctt    900
tgcgccgcct attaaggagg aactgatgga cgagattttg cttcactccc ctttggcgaa    960
tctggtgcag ataatcataa tgttgaccat cggatggatg ccggggtacc tgctcctgaa   1020
cgctacgggg cctaggaaat acaagggact gagcaatagc cactttaacc caaattcggc   1080
gttgttttct ccgaaggacc gtctggacat tatttggtcc gacattgggt ttttcgtggc   1140
cttggcctgc gtggtatatg cctgtgtgca gtttggattt caaacggtgg aaagtatta    1200 cctgctgccg tacatggtgg tcaattatca cctggtcctc atcacgtacc tgcagcacac   1260
ggacgtcttc atccccact tcgggggag cgagtggacg tggtttaggg cgcccttttg    1320
cacggtcgac cgatccttcg gctggctttt ggaccatacg tttcaccata tcagtgacac   1380
tcatgtgtgc caccacatct tcagcaagat gccgttctac cacgcgcagg aggcgagtga   1440
gcacattcgc aaggcgttgg gcgactatta tttgaaggat gatacccga tttggaaggc    1500
```

| | |
|---|---|
| attgtggcga agttataccc tgtgcaagta cgtggactcg gaggagacga cggtattcta | 1560 |
| caagcagcgg gcatag | 1576 |

<210> SEQ ID NO 3
<211> LENGTH: 2317
<212> TYPE: DNA
<213> ORGANISM: Nannochloropsis

<400> SEQUENCE: 3

| | |
|---|---|
| atggttgagc aaacgttacc gaccttgtcc cagatcaaga aagccatccc cgagaaatgc | 60 |
| ttccaggtac aacgcggagg gggtggaggg gggggagtg aagcagggg ggggagaac | 120 |
| gggtgataaa gagggatagg ttgagagaat ggaagaggga aaagggaaga agtgttgcaa | 180 |
| ggacgtggtg ttgcaaggac gtggtgtacc tgtgcgtacc cgacccgcgt gtccacaagc | 240 |
| tcgagcagtc cgaagcgctt tgtcacccct ctcaccacat atccctccct cctgtctcca | 300 |
| tttcctccct tcagaaatcc ctcctccgct ccttttacta catgctgagg gacttcgcgg | 360 |
| ccttggcggc actctacttt gtttatccca cagtgcaggc caagtatgga ttgcctggtt | 420 |
| tgtttgtgtg gtggaacctc gcaggtaggg agggagggag gatgagaggg aagagaattg | 480 |
| gggaaagcca tcgagccgtc ttatacgtct tctaggcact cacaaactct tctcccctcc | 540 |
| ctcctcccct tcctccccag cttttttcat gtggtgcctc ttcgtgatag ccacgattg | 600 |
| cggccatggc tccttctccg agtacaagtg gctcaatgac atatgcggtc acatttgcca | 660 |
| cgccccttg atggtgcctt actggccttg cagaaggta tgggagccag ccgccctcc | 720 |
| ctccttccct ccctccccc ttccctcgtt ttaatgacat gtcgatcatc tcattcattc | 780 |
| tatctctgcc tcccttcctc cctacctccc ccctccatc cctttcgcca gtcccaccgc | 840 |
| cttcaccaca tgtaccacaa ccacctgact aaggacatgt cacacccgtg gatgaccaag | 900 |
| gaggtgttcg aggtaggaag ggagggaggg cggatatgtt gttgggatga acgctataga | 960 |
| gaaggcacgg gcttgtttga tcctgtggca tacctcacgc cttccctccc tcccctccctc | 1020 |
| cctccctccc tttttttttca ggacttgacc ccattcgagc aggcgttgct ggagaacccg | 1080 |
| ctgtccctct tcatcaagta caccttcctt tacctctttg cgggcaagat ggatggcagg | 1140 |
| tatgaagagg gatgagggca gaggacggat gagggagagg acgggaagtc ggacacggag | 1200 |
| tgggctcgct tcttgtccca ctctcgattg ctcaccctcc ctccctccct ccctccctcc | 1260 |
| ctccctccct cccttccgtc tggacacagc catgtagttc cattctcccc cctcttcacc | 1320 |
| gacaccaagg agcgggtgca atgcgctgtg tcgacgctgg gtatggtcgt cgcaggcgcc | 1380 |
| cttgtgtaca tcgggctcga gggcgggaag gagggaggga tggcgaggat aggatccatt | 1440 |
| tatgtggtgc cgttgctggt gttcaatgcc tggatcacga tggtgacata cctgcagcac | 1500 |
| cacgatgagg acaccaaggt ttatgcagag ggggagtgga actacatcaa gggggccctg | 1560 |
| gagacgatcg accgcgaata cggcatgggg attgacggtg agtttatcat tggttaaata | 1620 |
| tattgtgaca actctaatta attgattact ttcatgtttt aattgacaat cgttctcgg | 1680 |
| tgatggtgag gacaccaagg tgacagtttc ccacagctct gtcttagcct caagactaag | 1740 |
| ctggcctcct ttcctcccgc cctcccttcc cttagacctc tcccacaata tcacggatgg | 1800 |
| ccacgtggcg caccacctct tcttcacgca gatcccgcac taccacctga cggcggccac | 1860 |
| ggccgctgtg agacaatgcc tgcaacctac ggggacctac aagaagagga ggagctggaa | 1920 |
| ttttctcgct cgtttcacgg agcttaacta ccgtttgaaa tacgtcgcgg gccagggcgt | 1980 |
| gctctcctat gtggattggg aggtaaggga aggaggaaga gcgaaggagt gagggaaaga | 2040 |

-continued

| | |
|---|---|
| gtgaggaaaa gtaaatatag atggagggtt tgcgagctca gctttcttcc ttctcaccct | 2100 |
| tgctcccctcc ctcgtcttgt aaccatcaca ggtcgctcgc aagacccctg cttccgccgt | 2160 |
| cacctcctct ttctcttcct cctcctcttc ctcccttccg gcagaggctg ctgtcaaggc | 2220 |
| ggctgctgcc gttcccgttg ctgctgttgc tgctcccgtc cgagaaggaa gaccaacacg | 2280 |
| caagcgctct cccacccgtt catcctcccc tccgtaa | 2317 |

<210> SEQ ID NO 4
<211> LENGTH: 1305
<212> TYPE: DNA
<213> ORGANISM: Nannochloropsis

<400> SEQUENCE: 4

| | |
|---|---|
| atgcacgtct accccgacaa gcacgaagtc attgtcagca tggagcccat ggtggaaggg | 60 |
| atgctctcga agctcctcct ccccacgggg gagaaggctt ggcaaccgtc cgactttgtc | 120 |
| ccggacctga ccaaggaagg gtgggaagac gaggtaaagg aattcaggga aaaggcggag | 180 |
| acgttgccgg acgagacgct ggtggtcttg gtggggggaca tggtgactga ggaggcgttg | 240 |
| cccacttacc agacgctgtt gaacacgttc gagggcgtgg atgaccccac cgggacgagt | 300 |
| ccttcggcct ggtgccgatg gacacggggg tggacgagcg aggagaacag gcacggggat | 360 |
| ctgctcaacc ggtacttgta cttgacgggg cgcgtggaca tgcgcgcgat cgagtgcacg | 420 |
| attcagcacc tggtacgtgg ggatgggagg gagggagaga gggagggatg gaggaaggct | 480 |
| cctgttcttg tgttcccccc cttcgtctcg cgcgatgtct aactcattct tcccacccctc | 540 |
| cctccctctg cgtccgtaaa ttagatttcg agcggttttca accccaaaat caagaaggat | 600 |
| ccgtacaagg gtttcgtata cacctccttc caagagcgag caaccaagat ctcccatcag | 660 |
| aatgtggcgc ggctggccaa cagcgccggt gatggcaatc tgggtctgat ctgcagtaag | 720 |
| attgcagggg atgagtcgag gcacgagaag gcataccaag ccatcttcca ggagatcctc | 780 |
| aagaaggacc cggaaggggg gttgaagagc ttctatgagt taatgagtga tcaggtaggg | 840 |
| agggcggagg agaggagggg ggaaagggag ggaggtaggt acgcattagg aggcaggagg | 900 |
| aagggaacga cacaagtact ttcaccatgg gccaagatac ggctgtttac ctttccctcc | 960 |
| tccctccctc tctccctccc tccctccctc cctccctcat ctcagatcac catgcctgcc | 1020 |
| gtgatgatga cggacgggca cgacccggac ctcttcgagc acttctcggt cacggcgcag | 1080 |
| aagctcggtg tctacacggc agtggactac gccaacattc tggaatattt ggtggagaca | 1140 |
| tgggacatcg agcacatggg aggcctgtct tctgaagggg ccaagtacca ggagaagctc | 1200 |
| tgcaagctcg cgccccgata catgaggctt gccgagatga gtcttgaccg ggtgaaaaag | 1260 |
| atgcccaaga cgccttattc ttggatccat ggacgcgtgg cttaa | 1305 |

<210> SEQ ID NO 5
<211> LENGTH: 1080
<212> TYPE: DNA
<213> ORGANISM: Nannochloropsis

<400> SEQUENCE: 5

| | |
|---|---|
| atggtcttcc agctcgcccg agactctgtc tcggccctgg tctatcattt caaagaagga | 60 |
| aaccttaact ggcctatgat tatctacctc gtccttgtcc acttggcggg ctacatcggt | 120 |
| ctgactacca ttctggcttg caaatggcaa actctcctcg aagcgttcat cctatggccc | 180 |
| atcaccgggc tggggattac tgccggcgta caccgacttt gggcacaccg ttcgtacaat | 240 |
| gccacgttgc cttatcgcat cctgttgatg ttgttcaact caattgcgaa ccaaggcagc | 300 |

-continued

```
atctaccact ggtcccggga ccaccgcgtg caccacaagt actccgagac tgatgctgac    360
ccacataacg ccaccgtgg cttcttcttc gcgcacatgg gctggctcat tgttaagaag     420
caccccaagg tcgtcgaagg ggggaagcaa ctcgatttct ccgatttggc tgccgatccc    480
gtggtgcgat tccagcgtga ttgggatccg tggttcgccc agtttatgtg ctttgtcatg    540
ccggcgcttg ttgcatcgag gttctggggt gaggcgttct ggaacgcctt tgggtggcg     600 ggggctttga ggtatatgtt ggtgctgcac ttcacctgga tggttaacag tgcggcgcac    660
ttgtatggcg accaccgta cgaccctacc atgtggccgg cggagaaccc gttggtatcg     720
gtagtggcga tcgagaaggg ctggcataac tggcaccatc gttaccccta cgactacgcg    780
gcttccgagt ttgggatttc gcagcagttc aacccgacca aggcgttcat tgatttttt     840 gcggccatag ggatggtgac gaaccgaaaa cgtgcgacgg gggcttgggc aaagctcaag    900
gaatccaggg caagggatgc ggcgaatggg aagagcatga aagatttcaa gggaagaggc    960
tcggggtcag actatggtac gacaaacacc aattacgcgg tgtcgaacaa gacagtggtg   1020
accgacaagg gggcgcaaca accagggtgg gaggagagca tcaccccaa gtacaactaa   1080
```

<210> SEQ ID NO 6
<211> LENGTH: 440
<212> TYPE: PRT
<213> ORGANISM: Nannochloropsis

<400> SEQUENCE: 6

```
Met Val Arg Gln His Lys Thr Pro Gln Asp Ala Trp Leu Val Tyr Arg
1               5                   10                  15

Asn Lys Val Tyr Asp Val Ser Gly Trp Gln Asp His Pro Gly Gly Asn
            20                  25                  30

Val Ile Phe Thr His Ala Gly Gly Asp Cys Thr Asp Ile Phe Ala Ala
        35                  40                  45

Phe His Pro Leu Gly Ala Thr Ser Tyr Leu Asp Pro Phe Tyr Ile Gly
    50                  55                  60

Glu Leu Glu Pro Gly Ser Asp Lys Lys Pro Ala Ala Gln Ala Asn Phe
65                  70                  75                  80

Glu Arg Ala Tyr Arg Asp Leu Arg Gly Lys Leu Ile Ala Gly Gly Phe
                85                  90                  95

Phe Lys Ala Asn Pro Leu Tyr Tyr Val Trp Lys Val Ser Thr Val
            100                 105                 110

Ala Leu Ala Val Gly Ala Trp Met Leu Val Ala Trp Ser Gln Asn Leu
        115                 120                 125

Gly Val Gln Met Leu Ser Ala Phe Leu Val Ala Leu Phe Trp Gln Gln
    130                 135                 140

Cys Gly Trp Leu Ala His Asp Phe Leu His Gln Val Phe Lys Asn
145                 150                 155                 160

Arg Ala Leu Gly Asp Leu Ala Gly Ile Val Ile Gly Asn Val Phe Gln
                165                 170                 175

Gly Phe Ser Val Ala Trp Trp Lys Asn Lys His Asn Thr His His Ala
            180                 185                 190

Val Pro Asn Leu Val Glu Ser Ser Pro Asp Ala Gln Asp Gly Asp Pro
        195                 200                 205

Asp Ile Asp Thr Met Pro Ile Leu Ala Trp Ser Leu Lys Met Ala Asp
    210                 215                 220

Arg Ala Gln Gln Tyr Ser Trp Gly Pro Phe Phe Val Arg His Gln Ser
225                 230                 235                 240

Leu Leu Tyr Phe Pro Ile Leu Leu Val Ala Arg Ile Ser Trp Leu Met
```

-continued

```
                    245                 250                 255
Gln Ser Phe Leu Phe Val Phe Asp Ser Val Pro Gly Ala Ser Leu Trp
            260                 265                 270

Ala Thr Lys Gly Ala Thr Ala Glu Arg Gln Ala Ile Lys Asn Val Gly
        275                 280                 285

Leu Glu Lys Val Gly Leu Val Ala His Tyr Leu Trp Tyr Gly Ala Leu
    290                 295                 300

Met Leu Cys His Met Ser Leu Ala Arg Ala Leu Leu Tyr Phe Leu Ala
305                 310                 315                 320

Ser Gln Met Met Cys Gly Phe Leu Leu Ala Leu Val Phe Gly Leu Gly
                325                 330                 335

His Asn Gly Met Ala Val Tyr Asp Ala Asp Ala Arg Pro Asp Phe Trp
            340                 345                 350

Lys Leu Gln Val Thr Thr Thr Arg Asn Val Thr Gly Ser Trp Leu Val
        355                 360                 365

Gln Trp Phe Cys Gly Gly Leu Gly Tyr Gln Val Asp His His Leu Phe
    370                 375                 380

Pro Met Ile Pro Arg His Arg Leu Gly Lys Leu His Gly Leu Val Glu
385                 390                 395                 400

Gly Phe Cys Lys Asp His Gly Val Lys Tyr His Glu Thr Asn Met Trp
                405                 410                 415

Glu Gly Thr Lys Glu Val Leu Ala His Leu Ser Ser Val Thr Lys Glu
            420                 425                 430

Phe Val Ala Asp Phe Pro Ala Met
        435                 440

<210> SEQ ID NO 7
<211> LENGTH: 438
<212> TYPE: PRT
<213> ORGANISM: Nannochloropsis

<400> SEQUENCE: 7

Met Gly Arg Gly Gly Glu Lys Thr Val Thr Pro Leu Arg Lys Lys Thr
1               5                   10                  15

Leu Leu Asp Ala Ala Ser Thr Ile Ser Gly Thr Val Arg Pro Ser Lys
            20                  25                  30

Ala Val Glu Ala Leu Pro Thr Glu Glu Leu Arg Lys Lys Ala Ala Gln
        35                  40                  45

Tyr Gly Ile Asn Thr Ser Val Asp Arg Glu Thr Leu Leu Arg Glu Leu
    50                  55                  60

Ala Pro Tyr Gly Asp Ile Leu Leu Arg Asn Asp Ala Pro Lys Ser Leu
65                  70                  75                  80

Pro Leu Ala Pro Pro Phe Thr Leu Ser Asp Ile Lys Asn Ala Val
                85                  90                  95

Pro Arg His Cys Phe Glu Arg Ser Leu Ser Thr Ser Leu Phe His Leu
            100                 105                 110

Thr Ile Asp Leu Ile Gln Val Ala Val Leu Gly Tyr Leu Ala Ser Leu
        115                 120                 125

Leu Gly His Ser Asp Val Pro Pro Met Ser Arg Tyr Ile Leu Trp Pro
    130                 135                 140

Leu Tyr Trp Tyr Ala Gln Gly Ser Val Leu Thr Gly Val Trp Val Ile
145                 150                 155                 160

Ala His Glu Cys Gly His Gln Ser Phe Ser Pro Tyr Glu Ser Val Asn
                165                 170                 175

Asn Phe Phe Gly Trp Leu Leu His Ser Ala Leu Leu Val Pro Tyr His
```

-continued

```
                    180                 185                 190
Ser Trp Arg Ile Ser His Gly Lys His His Asn Asn Thr Gly Ser Cys
                195                 200                 205
Glu Asn Asp Glu Val Phe Ala Pro Pro Ile Lys Glu Glu Leu Met Asp
            210                 215                 220
Glu Ile Leu Leu His Ser Pro Leu Ala Asn Leu Val Gln Ile Ile Ile
225                 230                 235                 240
Met Leu Thr Ile Gly Trp Met Pro Gly Tyr Leu Leu Asn Ala Thr
                245                 250                 255
Gly Pro Arg Lys Tyr Lys Gly Leu Ser Asn Ser His Phe Asn Pro Asn
            260                 265                 270
Ser Ala Leu Phe Ser Pro Lys Asp Arg Leu Asp Ile Ile Trp Ser Asp
            275                 280                 285
Ile Gly Phe Phe Val Ala Leu Ala Cys Val Val Tyr Ala Cys Val Gln
            290                 295                 300
Phe Gly Phe Gln Thr Val Gly Lys Tyr Tyr Leu Leu Pro Tyr Met Val
305                 310                 315                 320
Val Asn Tyr His Leu Val Leu Ile Thr Tyr Leu Gln His Thr Asp Val
                325                 330                 335
Phe Ile Pro His Phe Arg Gly Ser Glu Trp Thr Trp Phe Arg Gly Ala
                340                 345                 350
Leu Cys Thr Val Asp Arg Ser Phe Gly Trp Leu Leu Asp His Thr Phe
            355                 360                 365
His His Ile Ser Asp Thr His Val Cys His His Ile Phe Ser Lys Met
        370                 375                 380
Pro Phe Tyr His Ala Gln Glu Ala Ser Glu His Ile Arg Lys Ala Leu
385                 390                 395                 400
Gly Asp Tyr Tyr Leu Lys Asp Asp Thr Pro Ile Trp Lys Ala Leu Trp
                405                 410                 415
Arg Ser Tyr Thr Leu Cys Lys Tyr Val Asp Ser Glu Thr Thr Val
                420                 425                 430
Phe Tyr Lys Gln Arg Ala
            435

<210> SEQ ID NO 8
<211> LENGTH: 410
<212> TYPE: PRT
<213> ORGANISM: Nannochloropsis

<400> SEQUENCE: 8

Met Val Glu Gln Thr Leu Pro Thr Leu Ser Gln Ile Lys Lys Ala Ile
1               5                   10                  15
Pro Glu Lys Cys Phe Gln Lys Ser Leu Leu Arg Ser Phe Tyr Tyr Met
                20                  25                  30
Leu Arg Asp Phe Ala Ala Leu Ala Ala Leu Tyr Phe Val Tyr Pro Thr
            35                  40                  45
Val Gln Ala Lys Tyr Gly Leu Pro Gly Leu Phe Val Trp Trp Asn Leu
        50                  55                  60
Ala Gly Phe Phe Met Trp Cys Leu Phe Val Ile Gly His Asp Cys Gly
65                  70                  75                  80
His Gly Ser Phe Ser Glu Tyr Lys Trp Leu Asn Asp Ile Cys Gly His
                85                  90                  95
Ile Cys His Ala Pro Leu Met Val Pro Tyr Trp Pro Trp Gln Lys Ser
            100                 105                 110
His Arg Leu His His Met Tyr His Asn His Leu Thr Lys Asp Met Ser
```

```
                115             120             125
His Pro Trp Met Thr Lys Glu Val Phe Glu Asp Leu Thr Pro Phe Glu
130             135             140
Gln Ala Leu Leu Glu Asn Pro Leu Ser Leu Phe Ile Lys Tyr Thr Phe
145             150             155             160
Leu Tyr Leu Phe Ala Gly Lys Met Asp Gly Ser His Val Val Pro Phe
            165             170             175
Ser Pro Leu Phe Thr Asp Thr Lys Glu Arg Val Gln Cys Ala Val Ser
            180             185             190
Thr Leu Gly Met Val Val Ala Gly Ala Leu Val Tyr Ile Gly Leu Glu
            195             200             205
Gly Gly Lys Glu Gly Gly Met Ala Arg Ile Gly Ser Ile Tyr Val Val
210             215             220
Pro Leu Leu Val Phe Asn Ala Trp Ile Thr Met Val Thr Tyr Leu Gln
225             230             235             240
His His Asp Glu Asp Thr Lys Val Tyr Ala Glu Gly Glu Trp Asn Tyr
            245             250             255
Ile Lys Gly Ala Leu Glu Thr Ile Asp Arg Glu Tyr Gly Met Gly Ile
            260             265             270
Asp Asp Leu Ser His Asn Ile Thr Asp Gly His Val Ala His His Leu
            275             280             285
Phe Phe Thr Gln Ile Pro His Tyr His Leu Thr Ala Ala Thr Ala Ala
290             295             300
Val Arg Gln Cys Leu Gln Pro Thr Gly Thr Tyr Lys Lys Arg Arg Ser
305             310             315             320
Trp Asn Phe Leu Ala Arg Phe Thr Glu Leu Asn Tyr Arg Leu Lys Tyr
            325             330             335
Val Ala Gly Gln Gly Val Leu Ser Tyr Val Asp Trp Glu Val Ala Arg
            340             345             350
Lys Thr Pro Ala Ser Ala Val Thr Ser Ser Phe Ser Ser Ser Ser Ser
            355             360             365
Ser Ser Leu Pro Ala Glu Ala Val Lys Ala Ala Ala Val Pro
            370             375             380
Val Ala Val Ala Ala Pro Val Arg Glu Gly Arg Pro Thr Arg Lys
385             390             395             400
Arg Ser Pro Thr Arg Ser Ser Pro Pro
            405             410

<210> SEQ ID NO 9
<211> LENGTH: 333
<212> TYPE: PRT
<213> ORGANISM: Nannochloropsis

<400> SEQUENCE: 9

Met His Val Tyr Pro Asp Lys His Glu Val Ile Val Ser Met Glu Pro
1               5               10              15

Met Val Glu Gly Met Leu Ser Lys Leu Leu Pro Thr Gly Glu Lys
            20              25              30

Ala Trp Gln Pro Ser Asp Phe Val Pro Asp Leu Thr Lys Glu Gly Trp
            35              40              45

Glu Asp Glu Val Lys Glu Phe Arg Glu Lys Ala Glu Thr Leu Pro Asp
            50              55              60

Glu Thr Leu Val Val Leu Val Gly Asp Met Val Thr Glu Glu Ala Leu
65              70              75              80

Pro Thr Tyr Gln Thr Leu Leu Asn Thr Phe Glu Gly Val Asp Asp Pro
```

```
            85                  90                  95
Thr Gly Thr Ser Pro Ser Ala Trp Cys Arg Trp Thr Arg Gly Trp Thr
            100                 105                 110

Ser Glu Glu Asn Arg His Gly Asp Leu Leu Asn Arg Tyr Leu Tyr Leu
            115                 120                 125

Thr Gly Arg Val Asp Met Arg Ala Ile Glu Cys Thr Ile Gln His Leu
            130                 135                 140

Ile Ser Ser Gly Phe Asn Pro Lys Ile Lys Asp Pro Tyr Lys Gly
145                 150                 155                 160

Phe Val Tyr Thr Ser Phe Gln Glu Arg Ala Thr Lys Ile Ser His Gln
                    165                 170                 175

Asn Val Ala Arg Leu Ala Asn Ser Ala Gly Asp Gly Asn Leu Gly Leu
                180                 185                 190

Ile Cys Ser Lys Ile Ala Gly Asp Glu Ser Arg His Glu Lys Ala Tyr
                195                 200                 205

Gln Ala Ile Phe Gln Glu Ile Leu Lys Lys Asp Pro Glu Gly Gly Leu
            210                 215                 220

Lys Ser Phe Tyr Glu Leu Met Ser Asp Gln Ile Thr Met Pro Ala Val
225                 230                 235                 240

Met Met Thr Asp Gly His Asp Pro Asp Leu Phe Glu His Phe Ser Val
                    245                 250                 255

Thr Ala Gln Lys Leu Gly Val Tyr Thr Ala Val Asp Tyr Ala Asn Ile
                260                 265                 270

Leu Glu Tyr Leu Val Glu Thr Trp Asp Ile Glu His Met Gly Gly Leu
                275                 280                 285

Ser Ser Glu Gly Ala Lys Tyr Gln Glu Lys Leu Cys Lys Leu Ala Pro
            290                 295                 300

Arg Tyr Met Arg Leu Ala Glu Met Ser Leu Asp Arg Val Lys Lys Met
305                 310                 315                 320

Pro Lys Thr Pro Tyr Ser Trp Ile His Gly Arg Val Ala
                    325                 330

<210> SEQ ID NO 10
<211> LENGTH: 359
<212> TYPE: PRT
<213> ORGANISM: Nannochloropsis

<400> SEQUENCE: 10

Met Val Phe Gln Leu Ala Arg Asp Ser Val Ser Ala Leu Val Tyr His
1               5                   10                  15

Phe Lys Glu Gly Asn Leu Asn Trp Pro Met Ile Ile Tyr Leu Val Leu
                20                  25                  30

Val His Leu Ala Gly Tyr Ile Gly Leu Thr Thr Ile Leu Ala Cys Lys
            35                  40                  45

Trp Gln Thr Leu Leu Glu Ala Phe Ile Leu Trp Pro Ile Thr Gly Leu
        50                  55                  60

Gly Ile Thr Ala Gly Val His Arg Leu Trp Ala His Arg Ser Tyr Asn
65                  70                  75                  80

Ala Thr Leu Pro Tyr Arg Ile Leu Leu Met Leu Phe Asn Ser Ile Ala
                85                  90                  95

Asn Gln Gly Ser Ile Tyr His Trp Ser Arg Asp His Arg Val His His
            100                 105                 110

Lys Tyr Ser Glu Thr Asp Ala Asp Pro His Asn Ala Thr Arg Gly Phe
        115                 120                 125

Phe Phe Ala His Met Gly Trp Leu Ile Val Lys Lys His Pro Lys Val
```

-continued

```
            130                 135                 140
Val Glu Gly Gly Lys Gln Leu Asp Phe Ser Asp Leu Ala Ala Asp Pro
145                 150                 155                 160

Val Val Arg Phe Gln Arg Asp Trp Asp Pro Trp Phe Ala Gln Phe Met
                165                 170                 175

Cys Phe Val Met Pro Ala Leu Val Ala Ser Arg Phe Trp Gly Glu Ala
                180                 185                 190

Phe Trp Asn Ala Phe Trp Val Ala Gly Ala Leu Arg Tyr Met Leu Val
            195                 200                 205

Leu His Phe Thr Trp Met Val Asn Ser Ala Ala His Leu Tyr Gly Asp
        210                 215                 220

His Pro Tyr Asp Pro Thr Met Trp Pro Ala Glu Asn Pro Leu Val Ser
225                 230                 235                 240

Val Val Ala Ile Gly Glu Gly Trp His Asn Trp His His Arg Tyr Pro
                245                 250                 255

Tyr Asp Tyr Ala Ala Ser Glu Phe Gly Ile Ser Gln Gln Phe Asn Pro
                260                 265                 270

Thr Lys Ala Phe Ile Asp Phe Phe Ala Ala Ile Gly Met Val Thr Asn
            275                 280                 285

Arg Lys Arg Ala Thr Gly Ala Trp Ala Lys Leu Lys Glu Ser Arg Ala
        290                 295                 300

Arg Asp Ala Ala Asn Gly Lys Ser Met Lys Asp Phe Lys Gly Arg Gly
305                 310                 315                 320

Ser Gly Ser Asp Tyr Gly Thr Thr Asn Thr Asn Tyr Ala Val Ser Asn
                325                 330                 335

Lys Thr Val Val Thr Asp Lys Gly Ala Gln Gln Pro Gly Trp Glu Glu
                340                 345                 350

Ser Asn His Pro Lys Tyr Asn
            355
```